US007470720B2

(12) United States Patent
Littlefield et al.

(10) Patent No.: US 7,470,720 B2
(45) Date of Patent: *Dec. 30, 2008

(54) METHODS AND COMPOSITIONS FOR USE IN TREATING CANCER

(75) Inventors: Bruce A. Littlefield, Andover, MA (US); Murray J. Towle, Auburn, NH (US)

(73) Assignee: Eisai R&D Management Co., Ltd., Tokyo (JP)

( * ) Notice: Subject to any disclaimer, the term of this patent is extended or adjusted under 35 U.S.C. 154(b) by 456 days.

This patent is subject to a terminal disclaimer.

(21) Appl. No.: 10/687,526

(22) Filed: Oct. 16, 2003

(65) Prior Publication Data

US 2004/0198806 A1 Oct. 7, 2004

Related U.S. Application Data

(63) Continuation of application No. 10/272,167, filed on Oct. 16, 2002, now Pat. No. 6,653,341, which is a continuation-in-part of application No. 09/843,617, filed on Apr. 26, 2001, now Pat. No. 6,469,182, which is a continuation of application No. 09/677,485, filed on Oct. 2, 2000, now Pat. No. 6,365,759, which is a continuation of application No. 09/334,488, filed on Jun. 16, 1999, now Pat. No. 6,214,865.

(60) Provisional application No. 60/089,682, filed on Jun. 17, 1998, now abandoned.

(51) Int. Cl.
*A61K 31/335* (2006.01)
*C07D 407/00* (2006.01)

(52) U.S. Cl. ..................... 514/450; 549/414
(58) Field of Classification Search .............. 514/450
See application file for complete search history.

(56) References Cited

U.S. PATENT DOCUMENTS

| 5,338,865 | A | 8/1994 | Kishi et al. | |
|---|---|---|---|---|
| 5,436,238 | A | 7/1995 | Kishi et al. | |
| 6,214,865 | B1 * | 4/2001 | Littlefield et al. | ........... 514/450 |
| 6,365,759 | B1 | 4/2002 | Littlefield et al. | |
| 6,469,182 | B1 | 10/2002 | Littlefield et al. | |
| 6,653,341 | B1 * | 11/2003 | Littlefield et al. | ........... 514/450 |

FOREIGN PATENT DOCUMENTS

| EP | 0 572 109 A1 | 12/1993 |
|---|---|---|
| WO | WO 93/17690 | 9/1993 |

OTHER PUBLICATIONS

Campbell, M et al 'Pharmacokenetic optimisation of antiemetic therapy' PMID: 1355018 (1992).*
International Search Report for PCT/US03/32711.
Aicher et al., "Total Synthesis of Halichondrin B and Norhalichondron B," J. Am. Chem. Soc. 114:3162-3164 (1992).
Horita et al., "Synthetic Studies of Halichondrin B, and Antitumor Polyether Macrolide Isolated from a Marine Sponge. 8. Synthesis of the Lactone Part (C1-C36) via Horner-Emmons Coupling Between C1-C15 and C16-C36 Fragments and Yamaguchi Lactonization," Tetrahedron Letters 38:8965-8968 (1997).
Stamos et al., "New Synthetic Route to the C.14-C.38 Segment of Halichondrins," J. Org. Chem. 62:7552-7553 (1997).

\* cited by examiner

*Primary Examiner*—Janet L. Andres
*Assistant Examiner*—Raymond Covington
(74) *Attorney, Agent, or Firm*—Clark & Elbing LLP

(57) ABSTRACT

The invention provides methods and compositions for use in treating diseases associated with excessive cellular proliferation, such as cancer.

24 Claims, No Drawings

METHODS AND COMPOSITIONS FOR USE IN TREATING CANCER

CROSS-REFERENCE TO RELATED APPLICATIONS

This application is a continuation of, and claims priority from, U.S. patent application Ser. No. 10/272,167, filed Oct. 16, 2002, now U.S. Pat. No. 6,653,341, which is a continuation-in-part of, and claims priority from, U.S. patent application Ser. No. 09/843,617, filed Apr. 26, 2001 (now U.S. Pat. No. 6,469,182), which is a continuation of U.S. patent application Ser. No. 09/677,485, filed Oct. 2, 2000 (now U.S. Pat. No. 6,365,759), which is a continuation of U.S. patent application Ser. No. 09/334,488, filed Jun. 16, 1999 (now U.S. Pat. No. 6,214,865), which claims priority from U.S. Provisional Patent Application Ser. No. 60/089,682, filed Jun. 17, 1998 (now abandoned). The contents of the earlier filed applications are incorporated by reference herein in their entirety.

FIELD OF THE INVENTION

This invention relates to methods and compositions for use in treating cancer.

BACKGROUND OF THE INVENTION

Cancer is a term used to describe a wide variety of diseases that are each characterized by the uncontrolled growth of a particular type of cell. It begins in a tissue containing such a cell and, if the cancer has not spread to any additional tissues at the time of diagnosis, may be treated by, for example, surgery, radiation, or another type of localized therapy. However, when there is evidence that cancer has metastasized from its tissue of origin, different approaches to treatment are typically used. Indeed, because it is not possible to determine the extent of metastasis, systemic approaches to therapy are usually undertaken when any evidence of spread is detected. These approaches involve the administration of chemotherapeutic drugs that interfere with the growth of rapidly dividing cells, such as cancer cells.

Halichondrin B is a structurally complex, macrocyclic compound that was originally isolated from the marine sponge *Halichondria okadai*, and subsequently was found in *Axinella* sp., *Phakellia carteri*, and *Lissondendryx* sp. A total synthesis of halichondrin B was published in 1992 (Aicher et al., J. Am. Chem. Soc. 114:3162-3164, 1992). Halichondrin B has been shown to inhibit tubulin polymerization, microtubule assembly, beta$^S$-tubulin crosslinking, GTP and vinblastine binding to tubulin, and tubulin-dependent GTP hydrolysis in vitro. This molecule has also been shown to have anti-cancer properties in vitro and in vivo. Halichondrin B analogs having anti-cancer activities are described in U.S. Pat. No. 6,214,865 B1.

SUMMARY OF THE INVENTION

The invention provides methods of treating cancer in a patient, involving administration of a compound having the formula:

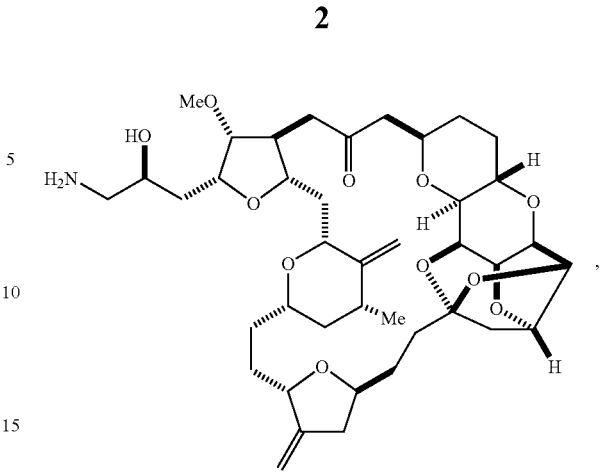

or a pharmaceutically acceptable salt thereof, which is carried out in combination with a second approach to treatment.

The second approach to treatment can involve administration of a chemotherapeutic drug to the patient. Examples of types of such drugs include antimetabolites, antibiotics, alkylating agents, plant alkaloids, and hormonal agents.

An antimetabolite, such as gemcitabine, can be used in the invention in the treatment of, for example, non-small cell lung carcinoma, pancreatic cancer, or metastatic breast cancer. An antimetabolite, such as capecitabine, can also be used in the invention in the treatment of, for example, breast cancer or colorectal cancer.

An example of a type of antibiotic that can be used in the invention is anthracyclines (e.g., doxorubicin), which can be used in the invention, for example, in the treatment of breast cancer.

Alkylating agents, such as, for example, carboplatinum or cisplatinum, can be used in the invention to treat, for example, non-small cell lung cancer or ovarian cancer.

Plant alkaloids, such as irinotecan and topotecan, can be used in the invention to treat, for example, colorectal cancer, ovarian cancer, or non-small cell lung carcinoma.

The second approach to treatment can also involve administration of an anticoagulant or antithrombotic agent (e.g., heparin) to the patient.

The invention also provides compositions that include a compound having the formula:

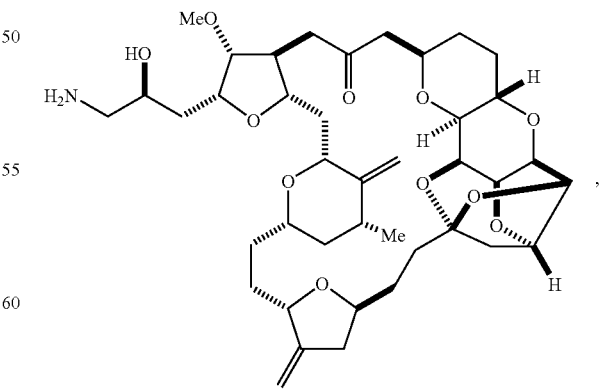

or a pharmaceutically acceptable salt thereof, in combination with a second anti-cancer drug. These drugs include, for example, any of the chemotherapeutic agents mentioned elsewhere herein, as well as others.

Other features and advantages of the invention will be apparent from the following detailed description and the claims.

DETAILED DESCRIPTION OF THE INVENTION

The invention provides methods for treating cancer, involving administration of a halichondrin B analog, such as an analog having the following structure:

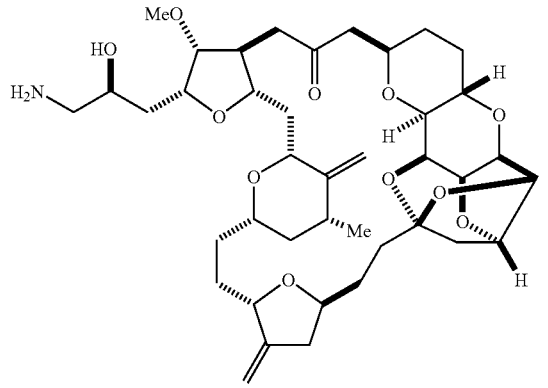

which is carried out in combination with a second approach to treatment.

There are numerous types of anti-cancer approaches that can be used in conjunction with halichondrin B analog treatment, according to the invention. These include, for example, treatment with chemotherapeutic agents (see below), biological agents (e.g., hormonal agents, cytokines (e.g., interleukins, interferons, granulocyte colony stimulating factor (G-CSF), macrophage colony stimulating factor (M-CSF), and granulocyte macrophage colony stimulating factor (GM-CSF)), chemokines, vaccine antigens, and antibodies), anti-angiogenic agents (e.g., angiostatin and endostatin), radiation, and surgery.

The methods of the invention can employ these approaches to treat the same types of cancers as those for which they are known in the art to be used, as well as others, as can be determined by those of skill in this art. Also, these approaches can be carried out according to parameters (e.g., regimens and doses) that are similar to those that are known in the art for their use. However, as is understood in the art, it may be desirable to adjust some of these parameters, due to the additional use of a halichondrin B analog with these approaches. For example, if a drug is normally administered as a sole therapeutic agent, when combined with a halichondrin B analog, according to the invention, it may be desirable to decrease the dosage of the drug, as can be determined by those of skill in this art. Examples of the methods of the invention, as well as compositions that can be used in these methods, are provided below.

Chemotherapeutic drugs of several different types including, for example, antimetabolites, antibiotics, alkylating agents, plant alkaloids, hormonal agents, anticoagulants, antithrombotics, and other natural products, among others, can be used in conjunction with halichondrin B treatment, according to the invention. Specific, non-limiting examples of these classes of drugs, as well as cancers that can be treated by their use, are as follows.

Antimetabolite drugs that halichondrin B analogs can be used with include, e.g., methotrexate, purine antagonists (e.g., mercaptopurine, thioguanine, fludarabine phosphate, cladribine, and pentostatin), and pyrimidine antagonists (e.g., gemcitabine, capecitabine, fluorouracil (e.g., 5-FU), cytarabine, and azacitidine). Use of these agents to treat particular types of cancers is well known in the art, and these agents can be used in combination with halichondrin B analogs to treat these and other types of cancers. As specific, non-limiting examples, a halichondrin B analog can be used with gemcitabine in the treatment of non-small cell lung carcinoma, pancreatic cancer, or metastatic breast cancer. In an additional example, a halichondrin B analog can be used in conjunction with capecitabine in the treatment of breast or colorectal cancers.

As is noted above, another class of chemotherapeutic drugs with which halichondrin B analogs can be used includes anticancer antibiotics. These include, for example, anthracyclines (e.g., doxorubicin, epirubicin, daunorubicin, and idarubicin), adriamycin, dactinomycin, idarubincin, plicamycin, mitomycin, and bleomycin. As with the drugs mentioned above, use of these agents to treat particular types of cancers is well known in the art, and they can be used in combination with halichondrin B analog treatment to treat these and other types of cancers. As a specific, non-limiting example, an anthracycline, such as doxorubicin, can be administered in conjunction with halichondrin B therapy for the treatment of breast or pancreatic cancers. Alternatively, a third agent, cyclophosphamide, can be used in this method.

Alkylating agents comprise another class of chemotherapeutic drugs that can be administered in conjunction with a halichondrin B analog, according to the invention. Examples of such drugs include procarbazine, dacarbazine, altretamine, cisplatin, carboplatin, and nitrosoureas. Halichondrin B analogs can be used with these agents in the treatment of cancers that these agents are known in the art to be used to treat, as well as in the treatment of other cancers. For example, a halichondrin B analog can be used in conjunction with carboplatinum in the treatment of non-small cell lung carcinoma or ovarian cancer.

An additional type of chemotherapeutic drug with which halichondrin B analogs can be administered, according to the invention, is plant alkaloids, such as vinblastine, vincristine, etoposide, teniposide, topotecan, irinotecan, paclitaxel, and docetaxel. As specific, non-limiting examples, a halichondrin B analog can be used in conjunction with irinotecan for the treatment of colorectal cancer, or with topotecan in the treatment of ovarian or non-small cell lung cancers.

Further types of anti-cancer agents that can be used in conjunction with halichondrin B analog treatment, according to the invention, are anticoagulants and antithrombotic agents. For example, heparin (e.g., low molecular weight heparin or heparin sulfate) or warfarin can be used. Use of these agents in treating patients by, for example, injection or oral administration, is well known in the art, and thus they can readily be adapted by those of skill in the art for use in the present invention.

Numerous approaches for administering anti-cancer drugs are known in the art, and can readily be adapted for use in the present invention. In the case of one or more drugs that are to be administered in conjunction with a halichondrin B analog, for example, the drugs can be administered together, in a single composition, or separately, as part of a comprehensive treatment regimen. For systemic administration, the drugs can be administered by, for example, intravenous infusion (continuous or bolus). Appropriate scheduling and dosing of such administration can readily be determined by those of skill in this art based on, for example, preclinical studies in animals and clinical studies (e.g., phase I studies) in humans. In addition, analysis of treatment using similar drugs, as well as monitoring factors such as blood counts (e.g., neutrophil and platelet counts) and vital signs in patients can be used, as is well understood in the art.

Many regimens used to administer chemotherapeutic drugs involve, for example, intravenous administration of a drug (or drugs) followed by repetition of this treatment after a period (e.g., 1-4 weeks) during which the patient recovers from any adverse side effects of the treatment. It may be desirable to use both drugs at each administration or, alternatively, to have some (or all) of the treatments include only one drug (or a subset of drugs).

As a specific, non-limiting example of a treatment regimen included in the invention, a halichondrin B analog (e.g., 0.01-5 mg/m$^2$) can be administered to a patient by intravenous infusion for 0.5-3 hours, followed by intravenous infusion of another drug (e.g., gemcitabine, e.g., 500-900 mg/m$^2$) for 0.5-3 hours. This course of treatment can be repeated every 2-3 weeks, as determined to be tolerable and effective by those of skill in the art. In a variation of this method, the treatment is carried out with both drugs on the first day, as is noted above, but then is followed up with treatment using only the secondary drug (e.g., gemcitabine) in ensuing weeks.

Further, as is well known in the art, treatment using the methods of the invention can be carried out in conjunction with the administration of antiemetics, which are drugs that are used to reduce the nausea and vomiting that are common side effects of cancer chemotherapy. Examples of such drugs include major tranquilizers (e.g., phenothiazines, such as chlorpromazine and prochlorperazine), dopamine antagonists (e.g., metoclopramide), serotonin antagonists (e.g., ondansetron and granisetron), cannabinoids (e.g., dronabinol), and benzodiazepine sedatives.

In addition to the cancers mentioned above, the methods and compositions of the invention can be used to treat the following types of cancers, as well as others: skin (e.g., squamous cell carcinoma, basal cell carcinoma, or melanoma), prostate, brain and nervous system, head and neck, testicular, lung, liver (e.g., hepatoma), kidney, bladder, gastrointestinal, bone, endocrine system (e.g., thyroid and pituitary tumors), and lymphatic system (e.g., Hodgkin's and non-Hodgkin's lymphomas) cancers. Other types of cancers that can be treated using the methods of the invention include fibrosarcoma, neurectodermal tumor, mesothelioma, epidermoid carcinoma, and Kaposi's sarcoma.

The invention also includes compositions that include a halichondrin B analog in combination with an additional therapeutic agent(s), such as any of those agents listed above. The drugs in these compositions preferably are formulated for administration to patients (e.g., in physiological saline) or, alternatively, can be in a form requiring further processing prior to administration. For example, the compositions can include the drugs in a lyophilized form or in a concentrated form requiring dilution. Formulation of drugs for use in chemotherapeutic methods can be carried out using standard methods in the art (see, e.g., *Remington's Pharmaceutical Sciences* (18$^{th}$ edition), ed. A. Gennaro, 1990, Mack Publishing Co., Easton, Pa.).

The invention features a compound having the formula (I):

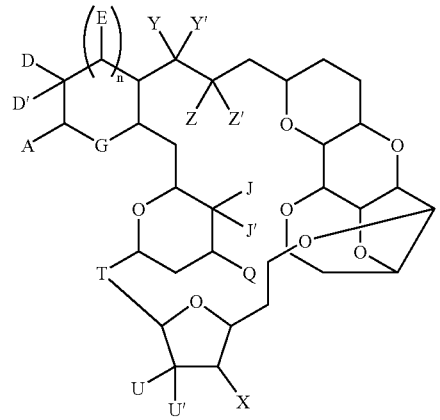

Formula (I)

In formula (I), A is a $C_{1-6}$ saturated or $C_{2-6}$ unsaturated hydrocarbon skeleton, the skeleton being unsubstituted or having between 1 and 13 substituents, preferably between 1 and 10 substituents, e.g., at least one substituent selected from cyano, halo, azido, $Q_1$, and oxo. Each $Q_1$ is independently selected from $OR_1$, $SR_1$, $SO_2R_1$, $OSO_2R_1$, $NR_2R_1$, $NR_2(CO)R_1$, $NR_2(CO)(CO)R_1$, $NR_4(CO)NR_2R_1$, $NR_2(CO)OR_1$,(CO)$OR_1$, $O(CO)R_1$, $(CO)NR_2R_1$, and $O(CO)NR_2R_1$. The number of substituents can be, for example, between 1 and 6, 1 and 8, 2 and 5, or 1 and 4. Throughout the disclosure, numerical ranges are understood to be inclusive.

Each of $R_1$, $R_2$, $R_4$, $R_5$, and $R_6$ is independently selected from H, $C_{1-6}$ alkyl, $C_{1-6}$ haloalkyl, $C_{1-6}$ hydroxyalkyl, $C_{1-6}$ aminoalkyl, $C_{6-10}$ aryl, $C_{6-10}$ haloaryl (e.g., p-fluorophenyl or p-chlorophenyl), $C_{6-10}$ hydroxyaryl, $C_{1-4}$ alkoxy-$C_6$ aryl (e.g., p-methoxyphenyl, 3,4,5-trimethoxyphenyl, p-ethoxyphenyl, or 3,5-diethoxyphenyl), $C_{6-10}$ aryl-$C_{1-6}$ alkyl (e.g., benzyl or phenethyl), $C_{1-6}$ alkyl-$C_{6-10}$ aryl, $C_{6-10}$ haloaryl-$C_{1-6}$ alkyl, $C_{1-6}$ alkyl-$C_{6-10}$ haloaryl, ($C_{1-3}$ alkoxy-$C_6$ aryl)-$C_{1-3}$ alkyl, $C_{2-9}$ heterocyclic radical, $C_{2-9}$ heterocyclic radical-$C_{1-6}$ alkyl, $C_{2-9}$ heteroaryl, and $C_{2-9}$ heteroaryl-$C_{1-6}$ alkyl. There may be more than one $R_1$, for example, if A is substituted with two different alkoxy ($OR_1$) groups such as butoxy and 2-aminoethyoxy.

Examples of A include 2,3-dihydroxypropyl, 2-hydroxyethyl, 3-hydroxy-4-perfluorobutyl, 2,4,5-trihydroxypentyl, 3-amino-2-hydroxypropyl, 1,2-dihydroxyethyl, 2,3-dihydroxy-4-perflurobutyl, 3-cyano-2-hydroxypropyl, 2-amino-1-hydroxy ethyl, 3-azido-2-hydroxypropyl, 3,3-difluoro-2,4-dihydroxybutyl, 2,4-dihydroxybutyl, 2-hydroxy-2(p-fluorophenyl)-ethyl, —CH$_2$(CO)(substituted or unsubstituted aryl),—CH$_2$(CO)(alkyl or substituted alkyl, such as haloalkyl or hydroxyalkyl) and 3,3-difluoro-2-hydroxypent-4-enyl.

Examples of $Q_1$ include —NH(CO)(CO)-(heterocyclic radical or heteroaryl),—OSO$_2$-(aryl or substituted aryl), —O(CO)NH-(aryl or substituted aryl), aminoalkyl, hydroxyalkyl, —NH(CO)(CO)-(aryl or substituted aryl), —NH(CO)(alkyl)(heteroaryl or heterocyclic radical), O(substituted or unsubstituted alkyl)(substituted or unsubstituted aryl), and —NH(CO)(alkyl)(aryl or substituted aryl).

Each of D and D' is independently selected from $R_3$ and $OR_3$, wherein $R_3$ is H, $C_{1-3}$ alkyl, or $C_{1-3}$ haloalkyl. Examples of D and D' are methoxy, methyl, ethoxy, and ethyl. In some embodiments, one of D and D' is H.

The value for n is 1 or preferably 0, thereby forming either a six-membered or five-membered ring. This ring can be unsubstituted or substituted, e.g., where E is $R_5$ or $OR_5$, and can be a heterocyclic radical or a cycloalkyl, e.g. where G is S, $CH_2$, $NR_6$, or preferably O.

Each of J and J' is independently H, $C_{1-6}$ alkoxy, or $C_{1-6}$ alkyl; or J and J' taken together are $=CH_2$ or —O-(straight or branched $C_{1-5}$ alkylene or alkylidene)-O—, such as exocyclic methylidene, isopropylidene, methylene, or ethylene. Q is $C_{1-3}$ alkyl, and is preferably methyl. T is ethylene or ethenylene, optionally substituted with $(CO)OR_7$, where $R_7$ is H or $C_{1-6}$ alkyl. Each of U and U' is independently H, $C_{1-6}$ alkoxy, or $C_{1-6}$ alkyl; or U and U' taken together are $=CH_2$ or —O-(straight or branched $C_{1-5}$ alkylene or alkylidene)-O—. X is H or $C_{1-6}$ alkoxy. Each of Y and Y' is independently H or $C_{1-6}$ alkoxy; or Y and Y' taken together are $=O$, $=CH_2$, or —O-(straight or branched $C_{1-5}$ alkylene or alkylidene)-O—. Each of Z and Z' is independently H or $C_{1-6}$ alkyl; or Z and Z' taken together are $=O$, $=CH_2$, or —O-(straight or branched $C_{1-5}$ alkylene or alkylidene)-O—.

The invention features pharmaceutical compositions which include a compound of formula (I) and a pharmaceutically-acceptable carrier. Compositions can also include a combination of disclosed compounds, or a combination of one or more disclosed compounds and other pharmaceutically-active agents, such as an anti-tumor agent, an immune-stimulating agent, an interferon, a cytokine, an anti-MDR agent or an anti-angiogenesis agent. Compositions can be formulated for oral, topical, parenteral, intravenous, or intramuscular administration, or administration by injection or inhalation. Formulations can also be prepared for controlled-release, including transdermal patches.

What is claimed is:

1. A pharmaceutical composition comprising a therapeutically effective amount of a compound having the formula:

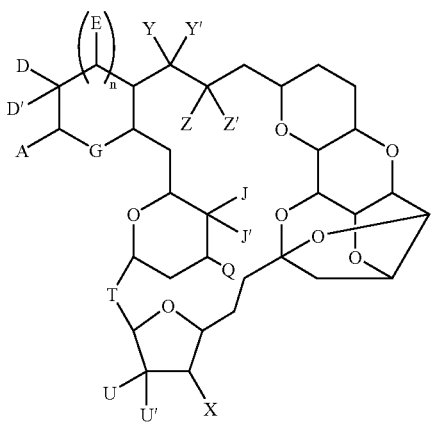

wherein A is a $C_{1-6}$ saturated or $C_{2-6}$ unsaturated hydrocarbon skeleton, said skeleton being unsubstituted or having between 1 and 10 substituents, inclusive, independently selected from cyano, halo, azido, oxo, and $Q_1$;

each $Q_1$ is independently selected from $OR_1$, $SR_1$, $SO_2R_1$, $OSO_2R_1$, $NR_2R_1$, $NR_2(CO)R_1$, $NR_2(CO)(CO)R_1$, $NR_4(CO)NR_2R_1$, $NR_2(CO)OR_1$, $(CO)OR_1$, $O(CO)R_1$, $(CO)NR_2R_1$, and $O(CO)NR_2R_1$;

each of $R_1$, $R_2$, $R_4$, $R_5$, and $R_6$ is independently selected from H, $C_{1-6}$ alkyl, $C_{1-6}$ haloalkyl, $C_{1-6}$ hydroxyalkyl, $C_{1-6}$ aminoalkyl, $C_{6-10}$ aryl, $C_{6-10}$ haloaryl, $C_{6-10}$ hydroxyaryl, $C_{1-3}$ alkoxy-$C_6$ aryl, $C_{6-10}$ aryl-$C_{1-6}$ alkyl, $C_{1-6}$ alkyl-$C_{6-10}$ aryl, $C_{6-10}$ haloaryl-$C_{1-6}$ alkyl, $C_{1-6}$ alkyl-$C_{6-10}$ haloaryl, ($C_{1-3}$ alkoxy-$C_6$ aryl)-$C_{1-3}$ alkyl, $C_{2-9}$ heterocyclic radical, $C_{2-9}$ heterocyclic radical-$C_{1-6}$ alkyl, $C_{2-9}$ heteroaryl, and $C_{2-9}$ heteroaryl-$C_{1-6}$ alkyl;

each of D and D' is independently selected from $R_3$ and $OR_3$, wherein $R_3$ is H, $C_{1-3}$ alkyl, or $C_{1-3}$ haloalkyl;

n is 0 or 1;

E is $R_5$ or $OR_5$;

G is O, S, $CH_2$, or $NR_6$;

each of J and J' is independently H, $C_{1-6}$ alkoxy, or $C_{1-6}$ alkyl; or J and J' taken together are $=CH_2$ or —O-(straight or branched $C_{1-5}$ alkylene)-O—;

Q is $C_{1-3}$ alkyl;

T is ethylene or ethenylene, optionally substituted with $(CO)OR_7$, where $R_7$ is H or $C_{1-6}$ alkyl;

each of U and U' is independently H, $C_{1-6}$ alkoxy, or $C_{1-6}$ alkyl; or U and U' taken together are $=CH_2$ or —O-(straight or branched $C_{1-5}$ alkylene)-O—;

X is H or $C_{1-6}$ alkoxy;

each of Y and Y' is independently H or $C_{1-6}$ alkoxy; or Y and Y' taken together are $=O$, $=CH_2$, or —O-(straight or branched $C_{1-5}$ alkylene)-O—; and each of Z and Z' is independently H or $C_{1-6}$ alkoxy; or Z and Z' taken together are $=O$, $=CH_2$ or —O-(straight or branched $C_{1-5}$ alkylene)-O—;

or a pharmaceutically acceptable salt thereof.

2. The pharmaceutical composition of claim 1, wherein n is 0.

3. The pharmaceutical composition of claim 1, wherein each of D and D' is independently selected from $R_3$, $C_{1-3}$ alkoxy, and $C_{1-3}$ haloalkyloxy.

4. The pharmaceutical composition of claim 1, wherein $R_5$ is selected from H, $C_{1-6}$ alkyl, $C_{1-6}$ haloalkyl, $C_{1-6}$ hydroxyalkyl, $C_{1-6}$ aminoalkyl, $C_{6-10}$ aryl, $C_{6-10}$ haloaryl, $C_{6-10}$ hydroxyaryl, $C_{1-3}$ alkoxy-$C_6$ aryl, $C_{6-10}$ aryl-$C_{1-6}$ alkyl, $C_{1-6}$ alkyl-$C_{6-10}$ is aryl, $C_{6-10}$ haloaryl-$C_{1-6}$ alkyl, $C_{1-6}$ alkyl-$C_{6-10}$ haloaryl, ($C_{1-3}$ alkoxy-$C_6$ alkyl)-$C_{1-3}$ alkyl, $C_{2-9}$ heterocyclic radical, $C_{2-9}$ heterocyclic radical-$C_{1-6}$ alkyl, $C_{2-9}$ heteroaryl, and $C_{2-9}$ heteroaryl-$C_{1-6}$ alkyl.

5. The pharmaceutical composition of claim 1, wherein A comprises a $C_{1-6}$ saturated or $C_{2-6}$ unsaturated hydrocarbon skeleton, said skeleton having at least one substituent selected from cyano, halo, azido, oxo, and $Q_1$;

each $Q_1$ is independently selected from $OR_1$, $SR_1$, $SO_2R_1$, $OSO_2R_1$, $NR_2R_1$, $NR_2(CO)R_1$, and $O(CO)NR_2R_1$;

n is 0;

G is O;

J and J' taken together are $=CH_2$;

Q is methyl;

T is ethylene;

U and U' taken together are $=CH_2$;

X is H;

each of Y and Y' is H; and

Z and Z' taken together are $=O$ or $=CH_2$.

6. The pharmaceutical composition of claim 1, wherein each $Q_1$ is independently selected from $OR_1$, $SR_1$, $SO_2R_1$, $OSO_2R_1$, $NH(CO)R_1$, $NH(CO)(CO)R_1$, and $O(CO)NHR_1$;

each $R_1$ is independently selected from $C_{1-6}$ alkyl, $C_{1-6}$ haloalkyl, $C_6$ aryl, $C_6$ haloaryl, $C_{1-3}$ alkoxy-$C_6$ aryl, $C_6$ aryl-$C_{1-3}$ alkyl, $C_{1-3}$ alkyl-$C_6$ aryl, $C_6$ haloaryl-$C_{1-3}$ alkyl, $C_{1-3}$ alkyl-$C_6$ haloaryl, ($C_{1-3}$ alkoxy-$C_6$ aryl)-$C_{1-3}$ alkyl, $C_{29}$ heterocyclic radical, $C_{2-9}$ heteroaryl, and $C_{2-9}$ heteroaryl-$C_{1-6}$ alkyl;

one of D and D' is methyl or methoxy, and the other is H;

n is 0;

G is O;

J and J' taken together are =$CH_2$;

Q is methyl;

T is ethylene;

U and U' taken together are =$CH_2$;

X is H;

each of Y and Y' is H; and

Z and Z' taken together are =O.

7. The pharmaceutical composition of claim 5, wherein A has at least one substituent selected from hydroxyl, amino, azido, halo, and oxo.

8. The pharmaceutical composition of claim 7, wherein A comprises a saturated hydrocarbon skeleton having at least one substituent selected from hydroxyl, amino and azido.

9. The pharmaceutical composition of claim 8, wherein A has at least two substituents independently selected from hydroxyl, amino, and azido.

10. The pharmaceutical composition of claim 8, wherein A has at least two substituents independently selected from hydroxyl and amino.

11. The pharmaceutical composition of claim 8, wherein A has at least one hydroxyl substituent and at least one amino substituent.

12. The pharmaceutical composition of claim 8, wherein A has at least two hydroxyl substituents.

13. The pharmaceutical composition of claim 8, wherein A comprises a $C_{2-4}$ hydrocarbon skeleton.

14. The pharmaceutical composition of claim 8, wherein A comprises a $C_3$ hydrocarbon skeleton.

15. The pharnmceutical composition of claim 13, wherein A has an (S)-hydroxyl on the carbon atom alpha to the carbon atom linking A to the ring containing G.

16. The pharmaceutical composition of claim 5, wherein A comprises a $C_{1-6}$ saturated hydrocarbon skeleton having at least one substituent selected from hydroxyl and cyano.

17. The pharmaceutical composition of claim 6, wherein $Q_1$ is independently selected from $OR_1$, $SR_1$, $SO_2R_1$, and $OSO_2R_1$ where each $R_1$ is independently selected from $C_{1-6}$ alkyl, $C_{1-6}$ haloalkyl, $C_6$ aryl, $C_6$ haloaryl, $C_{1-3}$ alkoxy-$C_6$ aryl, $C_6$aryl-$C_{1-3}$ alkyl, $C_{1-3}$ alkyl-$C_6$ aryl, $C_6$ haloaryl-$C_{1-3}$ alkyl, $C_{1-3}$ alkyl-$C_6$ haloaryl, and ($C_{1-3}$ alkoxy-$C_6$ aryl)-$C_{1-3}$ alkyl.

18. The pharmaceutical composition of claim 1, comprising a compound of the following structure or a pharmaceutically acceptable salt thereof.

19. The pharmaceutical composition of claim 1, comprising a compound of the following structure or a pharmaceutically acceptable salt thereof.

20. The pharmaceutical composition of claim 1, further comprising a pharmaceutically-acceptable carrier.

21. The pharmaceutical composition of claim 1, further comprising one or more other pharmaceutically-active agents.

22. The pharmaceutical composition of claim 21, wherein the one or more other pharmaceutically-active agents is selected from the group consisting of anti-tumor agents, immune-stimulating agents, interferons, cytokines, anti-MDR agents, and anti-angiogenesis agents.

23. The pharmaceutical composition of claim 1, wherein the pharmaceutical composition is formulated for administration by oral, topical, parenteral, intramuscular, or intravenous routes, or administration by injection or inhalation.

24. The pharmaceutical composition of claim 1, wherein the pharmaceutical composition is a controlled-release formulation.

* * * * *

UNITED STATES PATENT AND TRADEMARK OFFICE
CERTIFICATE OF CORRECTION

PATENT NO.        : 7,470,720 B2                                         Page 1 of 1
APPLICATION NO.   : 10/687526
DATED             : December 30, 2008
INVENTOR(S)       : Littlefield et al.

It is certified that error appears in the above-identified patent and that said Letters Patent is hereby corrected as shown below:

On the title page,

[*] Notice:   Subject to any disclaimer, the term of this patent is extended or adjusted under 35 USC 154(b) by (456) days Delete the phrase "by 456 days" and insert -- by 493 days --

Signed and Sealed this

Twenty-ninth Day of September, 2009

David J. Kappos
*Director of the United States Patent and Trademark Office*